United States Patent

Waldmann

[11] 3,931,816
[45] Jan. 13, 1976

[54] ADJUSTABLE ANTIPTOSIS CORSET

[76] Inventor: Jacobo Waldmann, 77 Espejo St., Mendoza, Argentina

[22] Filed: Jan. 7, 1975

[21] Appl. No.: 539,104

[52] U.S. Cl. ................................. 128/78; 128/579
[51] Int. Cl.² ......................................... A61F 5/02
[58] Field of Search ............ 128/78, 518, 521, 536, 128/580, 567, 568, 579, 95

[56] References Cited
UNITED STATES PATENTS

| | | | |
|---|---|---|---|
| 2,036,484 | 4/1936 | Le May | 128/78 |
| 2,354,697 | 8/1944 | Muller | 128/95 |
| 2,896,634 | 7/1959 | Beder | 128/579 R X |
| 3,234,937 | 2/1966 | Nelkin | 128/95 |
| 3,545,446 | 12/1970 | Nobbs | 128/78 X |

Primary Examiner—Richard A. Gaudet
Assistant Examiner—J. Yasko
Attorney, Agent, or Firm—Stevens, Davis, Miller & Mosher

[57] ABSTRACT

An adjustable antiptosis corset for human beings, to support viscera in general and to correct falling stomachs and the like in particular, comprising a resilient fabric to cover part of the rear and sides of the trunk of the bearer; the portion covering the rear is resilient in a vertical direction and the portions covering the sides are resilient in a horizontal direction, and a non-resilient ventral pocket member having a top access opening, said pocket member being connectable through adjustable self-fastening tapes to said side portions and which pocket member is provided with spaced-apart upstanding diverging whale-bone-like reinforcing members and separate parallel whale-bone-like reinforcing members, crossing said diverging whale-bone-like reinforcing members, and an unwrinkable, tapered cushion member having a thicker base portion, insertable in such pocket member, with said thicker base portion located on the bottom of said pocket member.

6 Claims, 11 Drawing Figures

U.S. Patent   Jan. 13, 1976   Sheet 1 of 2   3,931,816
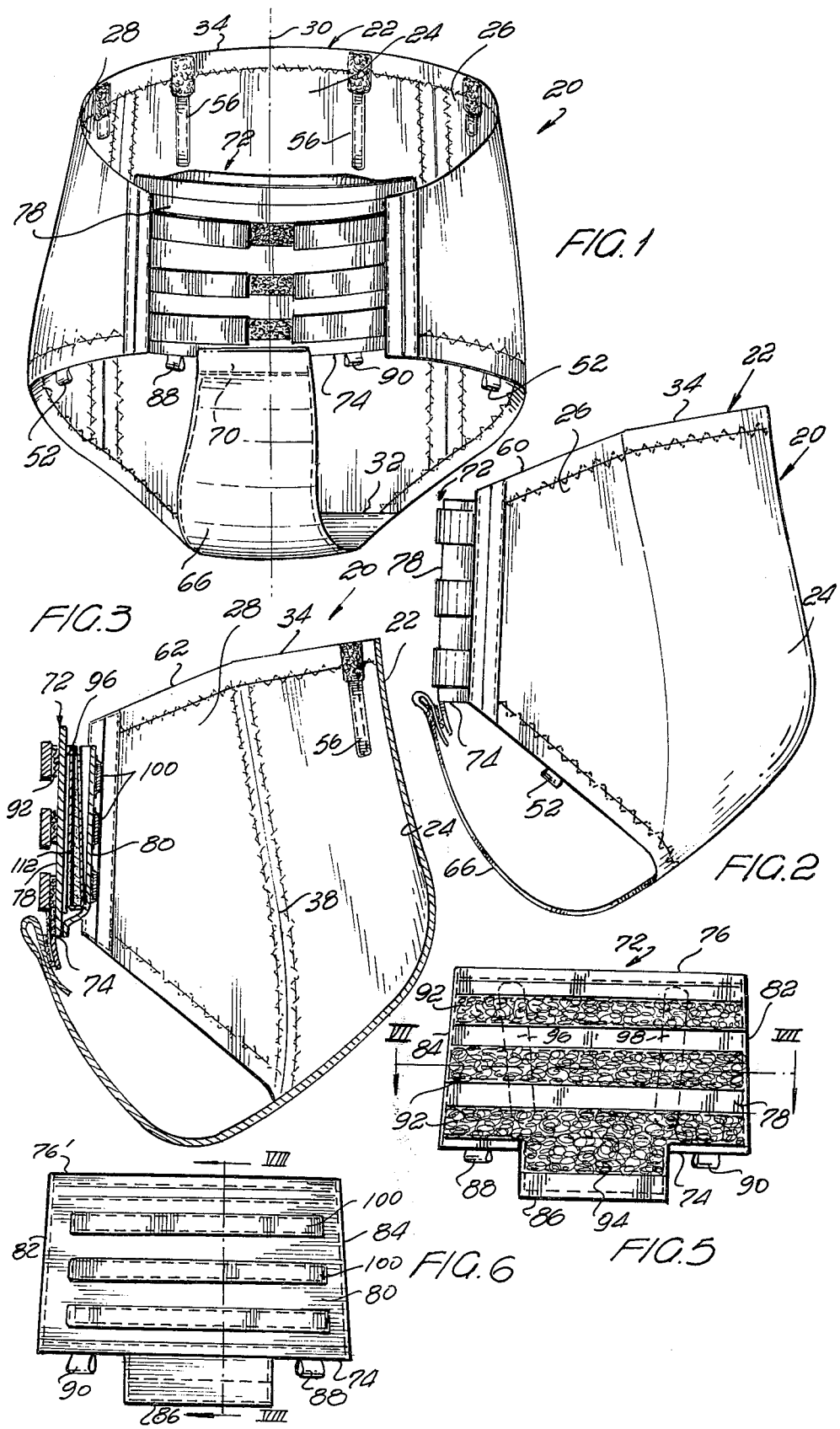

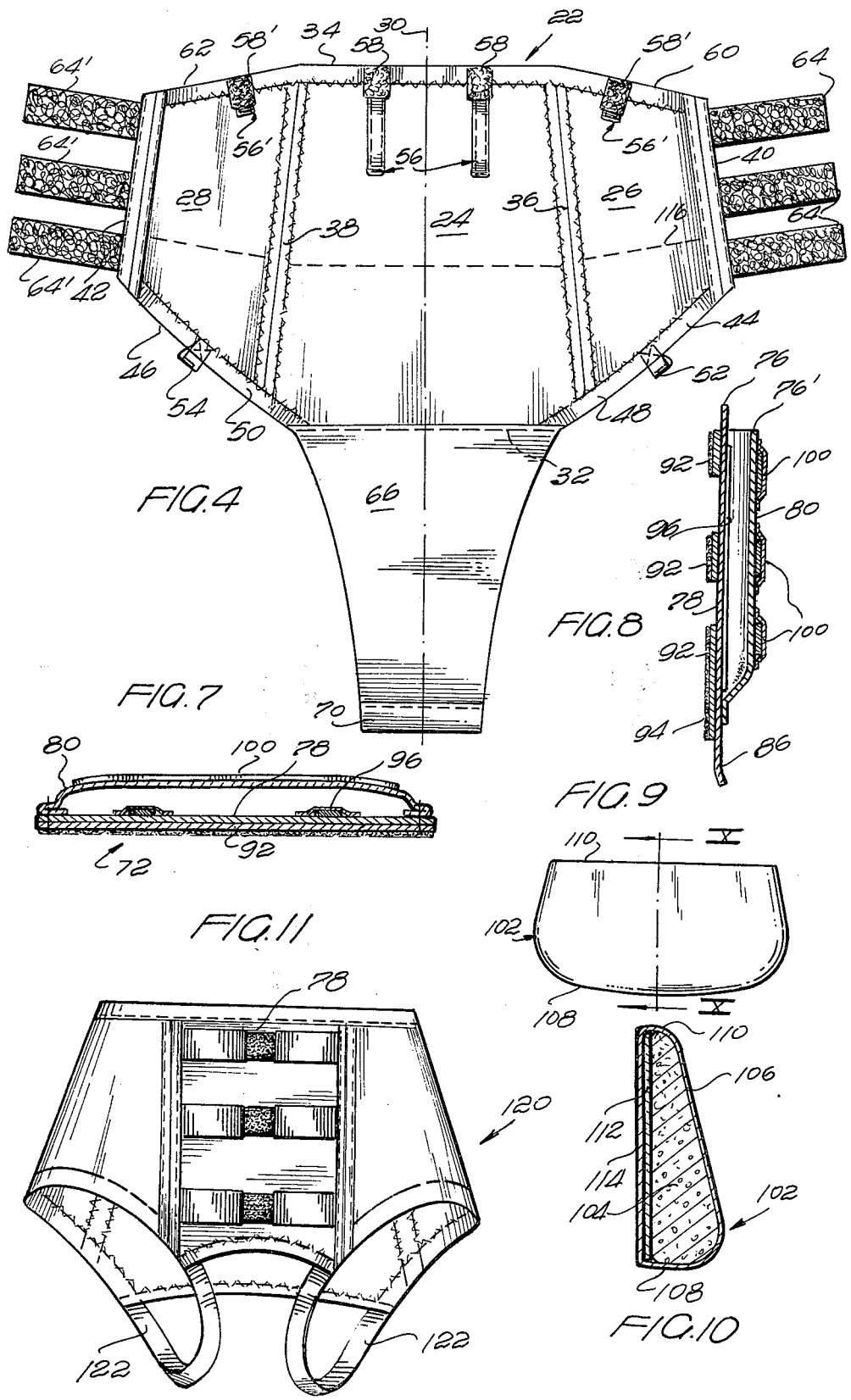

ADJUSTABLE ANTIPTOSIS CORSET

BACKGROUND OF THE INVENTION

1. Field of the Invention:

The present invention relates to an adjustable antiptosis corset to support viscera in general, to compensate distention, lowering, as well as slackness of muscles, tendons and ligaments supporting the stomach, intestine, kidney, womb and the like organs of the human being, in order to correct fallen stomachs and the like.

2. Description of the Prior Art.

Corsets as well as girdles for supporting viscera are already well known in the art, but most of the embodiments so far suggested have to be individually made, to obtain a proper adjustment and support to the viscera, in accordance with the size and other details of the patient. Frequently these corsets were unsatisfactory because upon the patient's physical condition changing (increasing or decreasing of weight), the corset did not provide proper support. Most of these corsets covered a portion of the body above the navel and thereby the pressure to be applied by the corset was not properly distributed. In view of the foregoing it is apparent that so far no proper garment of this type has been conceived which can be produced in standard sizes, to be adjusted for the first time by the physician or orthopedic, teaching thereby the wearer how to use the garment.

Thus the wearer can then carry out his or her own adjustments in accordance with physical variations, to which the human body may be subject.

SUMMARY OF THE INVENTION

According to the present invention there is provided an adjustable antiptosis corset to support viscera in general, to compensate distention, lowering, as well as slackness of muscles, tendons and ligaments supporting the stomach, intestine, kidney, womb and the like organs of the human being, in order to correct fallen stomach and the like, comprising a resilient fabric member to cover the rear and sides of part of the trunk of the wearer, and having a central portion and two side portions, said central portion being resilient in a generally vertical direction and said side portions being resilient in a generally horizontal direction with regard to the longitudinal axis of the human being, upon the corset being worn by the wearer, each side portion defining an outer substantial vertical edge, parallel clasp tape members projecting away at right angles from said outer edges, said central portion having a horizontal lower edge substantially perpendicular to said outer edges, a substantially trapezoidal ventral pocket member, having parallel larger and smaller edges, said pocket member including an outer non-resilient fabric wall member and an inner non-resilient fabric wall member linked together by their edges with the exception of the smaller adges which define a top access opening to the pocket formed by said fabric wall members, the said outer fabric wall member having an outer face provided with clasp linking means for said clasp tapes, and an inner face on which a pair of spaced apart, from bottom to top diverging whale-bone-like reinforcing members are mounted, said whale-bone-like reinforcing members diverging towards said top access opening, said inner non-resilient fabric wall member having parallel, whale-bone-like reinforcing members which are parallel to said parallel edges.

The corset of the present invention provides a particular arrangement of the above cited first resilient fabric member. More particularly, the central portion is larger towards its lower edge, whereby the side portions which are horizontally resilient can generate on the pocket member an inward pressure which decreases from the bottom of the pocket towards the access opening thereof. The particular resiliency of the central portion with regard to the side portions cooperates in achieving this purpose and at the same time assures that upon the wearer carrying out certain movements, such as bending the central portion, due to its resiliency in the vertical direction, follows such movement, whereas the side portions which are not resilient in the vertical direction, maintain on the pocket member the necessary inwardly directed supporting pressure on the pertinent organs.

The arrangement of the clasp tape members with the clasp linking means, which are of the self-fastening type, are preferably made of tapes, one series of which has on one side a fuzz-like nap, while the other series, i.e. the clasp linking means include hook-line projections. Thus upon pressing one tape of one series onto one tape of the other series, they become fastened. This type of self-fastening arrangement is known in the market under the trade-name "VELCRO", and may be easily adjusted by the wearer.

In addition, the pocket member may likewise be linked by its lower or bottom edge portion through such an adjustable self-fastening-type arrangement to a non-resilient crotch fabric member, further attached to the lower edge of the central portion of said first resilient fabric member.

BRIEF DESCRIPTION OF THE DRAWINGS

The invention is illustrated by way of example in the accompanying drawings, in which:

FIG. 1 is a perspective view, from the front, of the adjustable antiptosis corset, in accordance with the present invention.

FIG. 2, is a side elevation of the corset shown in FIG. 1.

FIG. 3, is a longitudinal section through the corset, as shown in FIG. 2.

FIG. 4, is a layout in plan view, showing the inside side of the first resilient fabric member, crotch fabric member and clasp tapes.

FIG. 5, is a plan view of the outside side of the pocket member.

FIG. 6, is a plan view of the inside side of the pocket member.

FIG. 7, is a cross-section along line VII—VII of FIG. 5

FIG. 8, is a longitudinal section, along line VIII—VIII of FIG. 6.

FIG. 9, is a plan view of the cushion member.

FIG. 10, is a cross-section along line X—X of FIG. 9.

FIG. 11, is a detail, in perspective view, showing another embodiment of the corset in accordance with the present invention, to be preferably used by males.

DESCRIPTION OF THE PREFERRED EMBODIMENTS

The adjustable antiptosis corset 20 of the present invention, as shown in FIG. 1, comprises a resilient fabric member 22, best shown in FIG. 4, having a central portion 24 and two side portions 26 and 28. The corset 20 as shown in FIG. 1 defines a longitudinal axis 30, which corresponds to such axis of the human being or wearer, who will use the corset 20, which in FIG. 1 is shown in its assembled position.

For convenience of explanation, the longitudinal axis 30 is likewise shown in FIG. 4. The central portion 24 is resilient in a general vertical direction, i.e. in a direction corresponding to axis 30. The central portion 24 has a horizontal lower edge 32, i.e. perpendicular to axis 30 and horizontal upper edge 34, which is smaller in length than the said lower horizontal edge 32. The side edges 36 and 38 define with said lower and upper edges 32, 34 a trapezoide. The side portions 26 and 28 have likewise an approximate trapezoidal shape, but the outer edges 40 and 42 are the parallel sides of the trapezoide with the side edges 36 and 38. The lower edges 44 and 46 are slightly curved and continue into the lower horizontal edge 32, by means of pertinent hems. The side portions 26 and 28 are resilient in a generally horizontal direction or in other words perpendicular to the longitudinal axis 30.

The fabric loop members 52, 54 are stitched to the hems 48, 50 for hooking in pertinent suspenders (not shown). Conveniently sheathed whale-bone arrangements 56 project downwardly from the horizontal upper edge 34 and are stitched on to the central portion 24 in the upper zone thereof, to avoid wrinkling of said zone. Conveniently the top portion of each whale-bone arrangement is covered with a soft cushion-like fabric. Similarly, the upper edges 60 and 62, of the side portions 26, 28 are provided with similar sheathed whale-bone arrangements 56', but which are smaller in length than the whale-bone arrangement 56 and likewise partially covered with cushion-like fabrics 58', for the same purpose. Three parallel clasp tape members 64, and 64' project away at right angles from each of said outer edges 40, 42.

The series of the clasp tape members 64, 64', have their inner faces covered with a fuzz-like nap and form part of a self-fastening arrangement, as will be explained later on. A non-resilient crotch fabric member 66, is attached to the lower edge 32 in the embodiment corresponding to FIGS. 1 to 4. The said non-resilient crotch fabric member 66 has likewise an approximate trapezoidal shape and the free edge 68 is covered on the inside side with a clasp-tape member 70, the purpose of which will be later explained.

A substantially trapezoidal ventral pocket member 72, which has parallel larger and smaller edges 74 and 76, 76' consists of an outer non-resilient fabric wall-member 78 and an inner non-resilient fabric wall member 80, linked together through stitching by the side edges 82, 84 and the larger edge 74, which thereby defines the bottom of the pocket member 72. Thus the smaller edge 76, 76' of the fabric wall member 78 and 80 define a top access opening of the pocket. The larger edge 74 comprises a tongue-like projection 86 at the central portion and adjacent thereto a pair of fabric loop-members 88 and 90 provided for the same purpose as loop members 52–54.

On the outer non-resilient wall member 78, and on the outside face thereof, clasp linking means are provided, consisting of three parallel tapes 92, each having projecting loops which define hook-like projections. These tapes 92 are stitched to member 78 and extend from side edge 82 to side edge 84.

A smaller clasp-linking tape 94 (FIG. 5) is stitched on the tongue-like projection 86, adjacent to the lowermost tape 92, whereby the free end portion of the tongue projection projects beyond the tape 94.

A pair, from bottom 74 to top 76 spaced-apart diverging whale-bone-like reiforcing members 96, 98 are mounted on the inner face of the outer non-resilient fabric wall member 78. Said whale-bone-like reiforcing members diverge towards said top access opening of the pocket. More particularly, these reinforcing members 96 and 98 have their lower end portions adjacent the side edges of the tongue-like projection 86 (see FIG. 5).

As best seen in FIGS. 3, 6 and 8, there are three parallel whale-bone-like reinforcing members 100, which are parallel to the edges 74 and 76', and attached to the inner non-resilient fabric wall member on the side remote from the pocket.

Finally, a cushion member 102, having a resilient filling 104 within a fabric casing 106 and being tapered from the bottom 108 towards the top 110, is insertable into the pocket with the bottom 108 to be arranged adjacent to the larger edge 74.

In order to avoid wrinkling of the said cushion member, a plate 112 is inserted in the cushion member and attached to the main side surface 114 thereof. The corset may be used with or without said cushion member 102.

When the patient uses the corset for the first time, the physician or orthopedic has to lay down the patient on a table with knees raised, in order that the lower portion of the abdomen becomes slightly raised with regard to the rest of the body.

The resilient fabric member 22 is of course to be placed firstly on the table so that the central portion 24 thereof becomes located below the lower portion of the back of the patient. Thereafter, the non-resilient crotch fabric member is inserted between the legs so that the free edge 68 becomes located on the pubis and then the pocket member 72 through its clasp-linking tape 94 and the clasp tape member 70 are pressed-fitted together. The combination of tapes 94 and 70 is known on the market under the trade-name "VELCRO". Thus, the pocket member 72 can be located on the belly with the upper edges 76, 76' below the navel of the patient. Thereafter, the clasp tape member 64, 64' are pressfitted on the clasp linking tapes 92 and thereafter pressure is applied on the clasp tape members 64, 64' to link them together. A suitable inwardly and upwardly directed pressure is thus exerted by the pocket-member 72 onto the abdomen. The pressure can be regulated by varying the position of the clasp tape members 64, 64' thereby slackening or tightening the assembly. The whale-bone-like reinforcing member 96, 98, 100 assure that no wrinkling takes place at the pocket member 72.

The lower-most clasp tape members 64 and 64' are under the influence, as far as the stress is concerned, of a larger zone of the side portions 26, 28 and central portion 24, namely the zone defined by the theoretical line 116 (FIG. 4), and the lower edges 44, 32, 46 than the remaining clasp tape member 64. The result is, that the pocket member will exert a greater pressure on the belly in the zone corresponding to the bottom of the pocket than in the zone corresponding to the top access opening of said pocket; still more specific, the pressure is decreasing from the bottom of the pocket towards the access opening of the pocket.

Depending on the specific diseases the patient is suffering, in some cases it may be advisable to insert in the pocket member the cushion member 102.

The fact that the central portion 24 is resilient in a generally vertical direction, assures that this portion of the corset can expand upon the wearer carrying out certain movements, such as bending and yet the cushion member will always be maintained in the same correct position, because the side portions 26, 28 are not resilient in the vertical direction, but only in the horizontal direction, thus maintaining the corset in the same position on the weaarer. In addition horizontally expandable side portions assure that the patient's diaphragm will not be hindered in its proper functioning during breathing.

Turning now to FIG. 11, the structural features of this embodiment are substantially the same as those previously described and the portion of the corset 120, there shown, differs from the corset 20 in that it has no crotch-fabric member.

Conveniently, the lower edges, which in the previous embodiment are identified by reference numerals 44, 46, form in this embodiment part of pertinent elastic ring members 122 to be fitted around the thighs of the wearer.

Although several embodiments of the invention have been described and illustrated in detail, it is to be expressly understood that the invention is not limited thereto. Various changes can be made in the design and arrangement of the parts, without departing from the spirit and scope of the invention, as the same will now be understood by those skilled in the art.

I claim:

1. An adjustable antiptosis corset to support viscera in general, to compensate distention, lowering, as well as slackness of muscles, tendons and ligaments supporting the stomach, intestine, kidney, womb and the like organs of the human being, in order to correct fallen stomachs and the like, comprising a resilient fabric member to cover the rear and sides of part of the trunk of the wearer, and having a central portion and two side portions, said central portion being resilient in a generally vertical direction and said side portions being resilient in a generally horizontal direction with regard to the longitudinal axis of the human being, upon the corset being worn by the wearer, each side portion defining an outer substantial vertical edge, parallel clasp tape members projecting away at right angles from said outer edges, said central portion having a horizontal lower edge substantially perpendicular to said outer edges, a substantially trapezoidal ventral pocket member, having parallel larger and smaller edges, said pocket member including an outer non-resilient fabric wall member and an inner non-resilient fabric wall member linked together by their edges with the exception of the smaller edges which define top access opening to the pocket formed by said fabric wall members, the said outer fabric wall member having an outer face provided with clasp linking means for said clasp tapes, and an inner face on which a pair of spaced apart, from bottom to top diverging whale-bone-like reinforcing members are mounted, said whale-bone-like reinforcing members diverging towards said top access opening, said inner non-resilient fabric wall member having parallel whale-bone-like reinforcing members which are parallel to said parallel edges.

2. The corset of claim 1, wherein a non-resilient crotch fabric member is attached to said lower edge and is of a substantially trapezoidal shape, said fabric member having an edge remote from said lower adge, and which is removably connected to said larger edge of said trapezoidal ventral pocket member.

3. The corset of claim 1, wherein said lower edges of said side portions are each stitched to an elastic ring member.

4. The corset of claim 1, wherein said parallel clasp tape members are covered on one side with a fuzz-like nap and said clasp linking means include hook-like projections, the fuzz-like naps being pressure fittable to said hook like projections.

5. The corset of claim 1, and further comprising a tapered cushion member insertable in said pocket member, said cushion member including a plate adapted to avoid wrinking of said cushion member.

6. The corset of claim 1, wherein said central portion is of a trapezoidal shape, said lower edge of said central portion, being parallel to the upper edge thereof, and said side portions being of trapezoidal shape and the respective outer edges being parallel to the side edge of said central portion and attached thereto.

* * * * *